United States Patent [19]  [11]  4,382,765
Möller et al.  [45]  May 10, 1983

[54] METHOD OF MOISTURIZING THE SKIN WITH CARBAMIDE ACID ESTERS

[75] Inventors: Hinrich Möller; Rainer Osberghaus; Manfred Budnowski, all of Düsseldorf, Fed. Rep. of Germany

[73] Assignee: Henkel Kommanditgesellschaft auf Aktien, Düsseldorf-Holthausen, Fed. Rep. of Germany

[21] Appl. No.: 206,974

[22] Filed: Nov. 14, 1980

Related U.S. Application Data

[63] Continuation of Ser. No. 873,220, Jan. 30, 1978, abandoned.

[30] Foreign Application Priority Data

Feb. 5, 1977 [DE] Fed. Rep. of Germany ....... 2704904

[51] Int. Cl.³ .................. A61K 7/42; A61K 7/15; A61K 47/00
[52] U.S. Cl. .................. 424/365; 252/110; 424/59; 424/73; 424/167; 424/359
[58] Field of Search .................. 424/272, 365; 560/160

[56] References Cited

U.S. PATENT DOCUMENTS

| | | | |
|---|---|---|---|
| Re. 29,607 | 4/1978 | Fauran et al. | 424/272 X |
| 1,927,858 | 9/1933 | Ulrich et al. | 560/160 |
| 1,933,945 | 11/1933 | Ulrich et al. | 560/160 |
| 2,528,398 | 10/1950 | Strain | 560/160 X |
| 2,755,286 | 7/1956 | Bell | 424/272 X |
| 2,772,281 | 11/1956 | Holly et al. | 424/272 X |
| 2,808,402 | 10/1957 | Boettner | 424/272 X |
| 2,831,858 | 4/1958 | de Benneville et al. | 424/272 X |
| 2,844,589 | 7/1958 | Hess | 424/272 X |
| 3,049,492 | 8/1962 | De Groote et al. | 424/272 X |
| 3,065,130 | 11/1962 | Walles | 424/272 X |

FOREIGN PATENT DOCUMENTS

| | | | |
|---|---|---|---|
| 269938 | 4/1913 | Fed. Rep. of Germany | 560/160 |
| 922708 | 1/1955 | Fed. Rep. of Germany | 560/160 |
| 1150973 | 7/1963 | Fed. Rep. of Germany | 560/160 |
| 1264432 | 3/1968 | Fed. Rep. of Germany | 560/160 |
| 508307 | 1/1955 | Italy | 560/160 |
| 309108 | 4/1929 | United Kingdom | 560/160 |
| 790796 | 2/1958 | United Kingdom | 560/160 |

Primary Examiner—Dale R. Ore
Attorney, Agent, or Firm—Hammond & Littell, Weissenberger and Muserlian

[57] ABSTRACT

Skin-care, skin-protection, and skin-cleaning agent compositions containing as a skin-moisturizing agent at least one substituted carbamide acid ester, said substituted carbamide acid ester having the formula

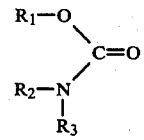

wherein $R_1$ is a member selected from the group consisting of an alkyl radical, having 1 to 4 carbon atoms, alkylol having 2 to 4 carbon atoms and alkyldiol having 3 to 4 carbon atoms, $R_2$ is a hydroxyalkyl having 2 to 6 carbon atoms and having 1 to 5 hydroxyl groups, or $R_2$, together with $R_1$, is an alkylene having 2 to 4 carbon atoms in its chain, which is optionally substituted by lower alkyl and/or lower hydroxyalkyl radicals, and $R_3$ is a member selected from the group consisting of hydrogen, alkyl having 1 to 4 carbon atoms and hydroxyalkyl having 2 to 4 carbon atoms, or an N-alkenyl polymer of the above cyclic carbamide acid ester, where $R_1$ and $R_2$ are alkylene and $R_3$ is alkenyl having 2 to 4 carbon atoms, as well as a process for protecting the skin utilizing this composition.

13 Claims, No Drawings

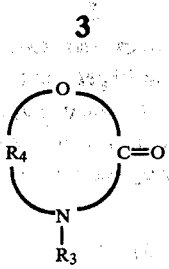

wherein $R_4$ is a member selected from the group consisting of linear alkylene having 2 to 4 carbon atoms, and alkylene of 2 to 4 carbon atoms substituted by a member selected from the group consisting of 1 or 2 alkyls having 1 to 4 carbon atoms, more preferably methyl groups; 1 or 2 hydroxyalkyls having 2 to 4 carbon atoms, more preferably hydroxymethyl groups; and a combination of said alkyl and hydroxyalkyl radicals. Advantageously, the hydrocarbon chain is substituted by one or two methyl groups, by one or two hydroxymethyl groups, or by a methyl and a hydroxymethyl group.

In addition the present invention provides a process for the care and protection of the skin of warm-blooded animals comprising topically applying to the skin a safe but effective amount of the agent composition mentioned above.

The substituted carbamide acid esters which are used in the agent compositions of the invention are extremely suitable for maintaining or restoring the water retention of the skin and thus for keeping the skin soft, flexible and fully capable of performing its function.

The compounds of the invention can be produced by generally known methods. Thus, for example, they can be obtained by reaction of chloroformic acid esters with corresponding primary or secondary amines or, alternatively, by reaction of carbamoyl chlorides with suitable alcohols in the presence of a base which binds hydrogen chloride. Furthermore, carbamide acid hydroxyalkyl esters are obtainable by aminolysis of a cyclic 5-, 6-, or 7-membered ring carbonate with a corresponding hydroxyalkyl amine. Cyclic carbamide acid esters may be obtained either by cyclocondensation of N-hydroxyalkyl-substituted ureas with the elimination of ammonia, or by condensation of hydroxyalkyl amines with carbonic acid esters, urea or phosgene.

Examples of compounds to be used in accordance with the invention are N-(2-hydroxybutyl)-, N-(1-hydroxy-2-methyl-2-propyl)-, N-(2-hydroxyethyl)-, N-(2-hydroxypropyl)-, N-(3-hydroxypropyl)-, N-(2,3-dihydroxypropyl)-, N-(1,3-dihydroxy-2-propyl)-, N-(1,3-dihydroxy-2-methyl-2-propyl)-, N-(1,3-dihydroxy-2-ethyl-2-propyl)-, N-(trishydroxymethyl-methyl)-, N-(2-hydroxyethyl)-N-methyl-, N-(2-hydroxy-propyl)-N-methyl, N-ethyl-N-(2,3-dihydroxypropyl)-, N-(2,3,4,5,6-pentahydroxyhexyl)-, N-(1,3,4,5-tetrahydroxy-2-pentyl)-, N,N-bis-(2-hydroxyethyl)-, N,N-(2-hydroxypropyl)-carbamide acid-methyl ester; -ethyl ester; -propyl ester; -2-propyl ester; -2-hydroxyethyl ester; -isobutyl ester; -2-hydroxypropyl ester; -3-hydroxypropyl ester; -2,3-dihydroxypropyl ester; ox-azolidone; N-methyl-, N-(2-hydroxyethyl)-, N-(2-hydroxypropyl)-, N-(3-hydroxypropyl)-, N-(2,3-dihydroxypropyl)-, 4-methyl-, 5-methyl-, 4,5-dimethyl-, 4,4-dimethyl-, 5,5-dimethyl-, N-(2-hydroxyethyl)-4-methyl-, N-(2-hydroxypropyl)-, 4,4-dimethyl-, 4-hydroxymethyl-, 5-hydroxymethyl-, 4-hydroxymethyl-4-methyl-, 4,4-bis-hydroxymethyl-, N-(2-hydroxypropyl)-5-methyl-oxazolidine-2-one; poly-N-vinyl-oxazolidine-2-one; tetrahydro-oxazine-2-one; hexahydro-oxazepin-2-one; N-(2-hydroxyethyl)-, N-(2-hydroxypropyl)-, 4,4-dimethyl-tetrahydro-oxazine-2-one.

The substituted carbamide acid esters of the invention are colorless to bright yellow colored, crystalline or highly viscous, fully stable products, which have very satisfactory physiological compatibility and, acting as neutral, nonionic compounds, are distinguished by the fact that they can be incorporated in cosmetic emulsion bases in a particularly satisfactory manner. Furthermore, it is not essential to produce the pure compounds; it is also possible to use the raw products of the preparative reaction when they are adjusted to a neutral pH value by treatment with an acid cation exchanger.

It was found that the functional capacity of the skin may be maintained or restored even to a higher degree than before if it is treated with agents for the care, protection, and cleaning of the skin, which besides the customary constituents include from 1% to 20% by weight, preferably 3% to 10% by weight, based on the total composition of the substituted carbamide acid esters or N-alkenyl polymer thereof in accordance with the invention.

Among the compositions for the care and protection of the skin having special skin-caring properties due to the addition of the substituted carbamide acid esters or N-alkenyl polymer thereof used in accordance with the invention are emulsions of the oil-in-water type or water-in-oil type.

Examples of agents for the care, protection and cleaning of the skin, to which special skin-care properties are imparted by the addition of the compounds of the invention are the conventional day creams, baby creams, night and nutrient creams, cleansing creams, skin protection creams, glycerol creams, creams having special additives of animal and vegetable origin, creams and emulsions for protection against the sun and sun tanning creams, soaps, bath oils, foam baths, shower baths, face lotions, and after-shave lotions. They can be incorporated in the agents for the care, protection and cleansing of the skin in a known manner simply by stirring-in or dissolving. In addition to the substituted carbamide acid esters or N-alkenyl polymer thereof used in accordance with the invention, the cosmetic preparations can also contain conventional quantities of the constituents usually contained therein, such as emulsifiers, fatty substances, vegetable extracts, thickeners, preservatives, surfactants, perfumes and solvents. Water and lower alcohols, such as methanol, ethanol and isopropanol, serve as very useful constituents of the cosmetic preparations of the invention. Lower alcohols of 1–3 carbon atoms are very suitable. The pH value of the agents for the care and protection of the skin may be in the range of acid to neutral (approximately pH 5–7.0) and, advantageously, is adjusted to a weakly acid value of approximately pH 6. The skin cleansing agents based on soap should be adjusted so as to have as weak an alkaline pH value as possible.

The following examples are intended to illustrate the subject of the invention without, however, limiting it to these examples.

EXAMPLES

Among the substituted carbamide acid esters, which are used in accordance with the invention as agents for keeping the skin moist, the following compounds were subjected to the tests described below and were used in

METHOD OF MOISTURIZING THE SKIN WITH CARBAMIDE ACID ESTERS

This is a continuation of Ser. No. 873,220, filed Jan. 30, 1978, now abandoned.

THE PRIOR ART

It is generally known that the protective measures for healthy skin include, among other things, that the skin surface maintains a certain hygroscopicity. When the substances, on which this hygroscopicity and its continuous restoration are based, are removed from the skin by environmental influences, such as repeated washing with substances having highly wetting and extracting effects, chemical influences and the strong effects of weathering, the epidermis is subjected to changes which can greatly reduce the protective action of the skin against injurious environmental influences.

Therefore, the task arose of providing cosmetic agents, particularly agents for the care, protection and cleaning of the skin, by means of which the ability of the skin to function is fully maintained or enhanced despite the injurious environmental influences, and by means of which the restoration of the epidermis is effectively assisted when damage to the skin has occurred.

The products hitherto used as agents for keeping the skin moist were, without exception, ionic compounds such as acids and, primarily salts, which, although they produced reliable results as skin moisture regulators in many cases, frequently caused difficulties when incorporated in the cosmetic preparations, especially in considerably reducing their stability, particularly of highly fluid oil/water emulsions. In such cases, it was frequently not possible to incorporate fully adequate quantities of skin moisture regulators. Furthermore, in addition to the general task of developing satisfactory agents for keeping the skin moist, a particular interest was attached to developing products which do not cause any difficulties such as stability problems, even when they are incorporated in oil/water emulsions.

OBJECTS OF THE INVENTION

It is an object of the present invention to provide a skin-care, skin-protection, and skin-cleaning agent composition containing at least one substituted carbamide acid ester or N-alkenyl polymer thereof as a skin moisturizing agent.

It is another object of the present invention to provide a skin-care and skin-protection agent composition, by means of which the functional capacity of the skin may be maintained or increased in spite of harmful environmental influences, and which effectively supports the restoration of the horny layer, should any damage have been incurred.

These and further objects of the invention will become apparent as the description thereof proceeds.

DESCRIPTION OF THE INVENTION

The present invention relates to skin-care, skin-protection and skin-cleaning agent compositions containing at least one substituted carbamide acid ester or N-alkenyl polymer thereof as a skin moisturizing agent.

Accordingly, the present invention involves cosmetic agents, particularly agents for the care, protection and cleaning of the skin, comprising conventional constituents, such as surfactants, emulsifiers, fatty substances, vegetable extracts, solvents, perfumes, thickening agents, and preservatives, and from 1 to 20 percent by weight, preferably 3 to 10 percent by weight, relative to the total weight of the cosmetic agent, of at least one substituted carbamide acid ester, said substituted carbamide acid ester having the formula

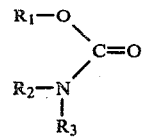

wherein $R_1$ is a member selected from the group consisting of an alkyl radical, having 1 to 4 carbon atoms, alkylol having 2 to 4 carbon atoms and alkyldiol having 3 to 4 carbon atoms, $R_2$ is a hydroxyalkyl having 2 to 6 carbon atoms and having 1 to 5 hydroxyl groups, or $R_2$ together with $R_1$, is an alkylene having 2 to 4 carbon atoms in its chain, which is optionally substituted by lower alkyl and/or lower hydroxyalkyl radicals, and $R_3$ is a member selected from the group consisting of hydrogen, alkyl having 1 to 4 carbon atoms and hydroxyalkyl having 2 to 4 carbon atoms, or an N-alkenyl polymer of the above cyclic carbamide acid ester, where $R_1$ and $R_2$ are alkylene and $R_3$ is alkenyl having 2 to 4 carbon atoms.

More particularly, the present invention provides a cosmetic agent composition for the care and protection of the skin of warm blooded animals consisting essentially of from 1% to 20% by weight based upon the total weight of at least one member selected from the group consisting of (i) a substituted carbamide acid ester, said substituted carbamide acid ester having the formula

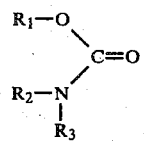

wherein $R_1$ is a member selected from the group consisting of an alkyl radical, having 1 to 4 carbon atoms, alkylol having 2 to 4 carbon atoms and alkyldiol having 3 to 4 carbon atoms, $R_2$ is a hydroxyalkyl having 2 to 6 carbon atoms and having 1 to 5 hydroxyl groups, or $R_2$ together with $R_1$, is an alkylene having 2 to 4 carbon atoms in its chain, which is optionally substituted by lower alkyl and/or lower hydroxyalkyl radicals, and $R_3$ is a member selected from the group consisting of hydrogen, alkyl having 1 to 4 carbon atoms and hydroxyalkyl having 2 to 4 carbon atoms, and (ii) an N-alkenyl polymer of the above cyclic carbamide acid ester, where $R_1$ and $R_2$ are alkylene and $R_3$ is alkenyl having 2 to 4 carbon atoms; and the remainder conventional cosmetic excipients.

In a special embodiment of the invention, the heterocyclic ring compounds have the formula formulations described below. The production of the compounds will be described in the first instance.

(A) N-(2-hydroxyethyl)-carbamide acid-2-hydroxyethyl ester

This compound was prepared from ethylene carbonate and ethanolamine in a 1:1 molar ratio in accordance with the method described in U.S. Pat. No. 2,441,298. The compound was obtained in the form of a light yellow oil having a refractive index $n_D^{20}$: 1.4783.

(B) N-(2-hydroxypropyl)-carbamide acid-2-hydroxyethyl ester 75 gm (1 mole) of isopropanolamine were added dropwise to an ethereal solution of 88 gm (1 mole) of ethylene carbonate under agitation and cooling. The addition was performed sufficiently slowly to prevent the temperature from exceeding 20° C. The mixture was subsequently agitated for 10 hours at boiling temperature, the ether was then distilled off and the residue was dried in vacuo. An almost quantitative yield of N-(2-hydroxypropyl)-carbamide acid-2-hydroxyethyl ester was obtained in the form of a colorless oil having a refractive index $n_D^{20}$: 1.4710.

The following were produced in an analogous manner:

(C) N-(1-hydroxy-2-methyl-2-propyl)-carbamide acid-2-hydroxyethyl ester

Colorless resin, $n_D^{20} = 1.4646$.

(D) N-(2-Hydroxyethyl)-carbamide acid-1-hydroxy-2-propyl ester $n_D^{20}$: 1.4725, b.p. 155° C./0.05 torr.

(E) N-(2-hydroxypropyl)-carbamide acid-1-hydroxy-2-propyl ester b.p. 152° to 153° C./0.01 torr, $n_D^{20}$: 1.4696.

The following compounds F to H were produced from urea and hydroxyalkylamines in accordance with the method described in U.S. Pat. No. 2,399,118.

(F) 4,4-Dimethyl-oxazolidine-2-one b.p. 107° to 109° C./0.01 torr; m.p. 48° to 50° C.

(G) 4-hydroxymethyl-4-methyl-oxazolidine-2-one m.p. 115° C.

(H) 4,4-bis-hydroxymethyl-oxazolidine-2-one

M.P. 106° to 108° C.

(I) N-(2-hydroxyethyl)-oxazolidine-2-one

This compound was prepared from diethylcarbonate and diethanolamine in accordance with the method of E. K. Drechsel in the Journal of Organic Chemistry 22 (1957), page 851. A clear, slightly colored liquid having a boiling point of 154° was obtained.

(J) Poly-N-vinyl-oxazolidine-2-one

This compound was produced by way of the monomeric N-vinyl-2-oxazolidine-2-one in accordance with the method of E. K. Drechsel in the Journal of Organic Chemistry 22 (1957), page 851. A solid, white, water-soluble product was obtained which sintered at 170° to 175° C. and exhibited incipient decomposition at 270° C.

The above products B, C and E are novel compounds not previously described as such.

The favorable action of the compounds, which are to be used in accordance with the invention, with respect to their capacity for the absorption and retention of water, was established by means of the test methods described hereinafter. A process for determining the equilibrium dampness which is indicative of the water retention capacity, and the determination of the water retention, rehydration and elasticity of impregnated pig epidermis are described in these tests.

1. DETERMINATION OF THE EQUILIBRIUM DAMPNESS

The substances (approximately 300 to 500 mg) to be tested were moistened with a defined quantity of water and were exposed for 24 hours at 23° C. to various relative atmospheric humidities (1%, 30%, 47%, 65%, 89% and 100% relative humidity). The quantity of water absorbed or desorbed was determined gravimetrically and plotted on a graph. The relative humidity at which neither expulsion nor retention of water is effected can be determined from the resultant curves. This value, which is designated as the "equilibrium dampness", is a measure of the water retention capacity of a substance. The lower the value, the more positive is the assessment of the product. Furthermore, the hygroscopicity of the substance can be read from the slope of the curve.

2. MEASUREMENTS MADE ON THE PIG EPIDERMIS (a) Obtainment of the pig epidermis Immediately after the pigs have been killed, the skin bristles are cut off by means of a shearing machine (shearing head 0.1 mm). The pigs are soaked for approximately 3 to 5 minutes in warm water of 60° C., the epidermis is subsequently peeled off and stored at −20° C. until it is used.

(b) Determination of the water retention and the rehydration of impregnated pig epidermis Stamped out pieces of epidermis (1×2 cm) were soaked for two hours in a 10% solution of the test substance. Excess moisture was then removed under standardized conditions by means of a small press, and the pieces were dried for 24 hours, hanging freely between 2 clamps in a 100 ml Erlenmeyer flask at 23° C., both at 30% relative humidity and 50% relative humidity (set by mixtures of sulfuric acid and water). The drying out of the impregnated test pieces to X% of the initial weight was compared with the corresponding value of the epidermis which had been soaked only in water (blank value). In Table I, the improvement in the water retention and in the rehydration as compared with the blank value is given in Δ% H₂O. The deviations in each double test amounted to a maximum of ±2 absolute units. The test was repeated if greater deviations occurred. The rehydration was determined analogously by drying the pig epidermis, which had been impregnated and from which the excess moisture had been removed, for 24 hours at 30% relative humidity, and by subsequent incubation for 24 hours at 90% relative humidity.

(c) Elasticity measurements made on the impregnated pig epidermis

Stamped out pieces of pig epidermis (1×6 cm) were soaked for two hours in a 10% aqueous solution of the substance which was to be tested, and excess moisture was removed from these pieces under standardized conditions. The test pieces were incubated for 24 hours, hanging freely between two clamps, both at 70% relative humidity and at 90% relative humidity, and, were stretched in a nipping tensile-testing machine (type: 1402) under a load of 0 to 50 pund. The amount of stretch in mm, measured in the Hooke range at a load between 5 to 30 pund, was determined as a measure of the elasticity.

The measured values obtained in the tests described above are given in the following Table I.

TABLE I

Equilibrium dampness and measured values for pig epidermis

| | | Measurements made on pig epidermis | | | |
|---|---|---|---|---|---|
| | Equilibrium dampness | Water Retention % H$_2$O after drying out | | Rehydration Δ% water absorption | mm stretch with between 5 and 30 pound loading |
| Product | (% r.h.) | at 30% r.h. | at 50% r.h. | at 90% r.h. | at 90% r.h.   at 75% r.h. |
| Blank value | — | 0 | 0 | 0 | 0.3-0.5   0 |
| A | 58 | 25 | 26 | 62 | 5.5   1.1 |
| B | 58 | 23 | 22 | 70 | 6.0   1.0 |
| F | 83 | 5 | 7 | 5 | 7.4   0.4 |
| H | 76 | 12 | 15 | 10 | 2.6   0.5 |
| I | 68 | 10 | 16 | 16 | 6.0   0.8 |
| J | 67 | 9 | 14 | 37 | 3.1   0.4 |

The above Table indicates, besides the strong hygroscopicity, also the considerable water retention capacity of the compounds used in accordance with the present invention, and thus demonstrates their eminent suitability for use as agents for keeping the skin moist in compositions for the care, protection and cleansing of the skin.

Some examples of cosmetic preparations, containing the substances for use in accordance with the invention as agents for keeping the skin moist, are given hereinafter.

EXAMPLE 1

| Day cream, slightly greasy | Parts by Weight |
|---|---|
| Fatty acid partial glyceride Cutina MD ® Dehydag | 6.0 |
| Stearic acid | 8.0 |
| Mixture of nonionic emulsifiers Emulgin C 700 ® Dehydag | 3.0 |
| 2-octyldodecanol | 4.0 |
| Vegetable oil | 3.0 |
| Paraffin oil | 5.0 |
| Triethanolamine | 0.4 |
| 1,2-propylene glycol | 3.0 |
| Product A | 6.0 |
| Nipagin M | 0.2 |
| Perfume oil | 1.0 |
| Water | 60.4 |

EXAMPLE 2

| Baby Cream | Parts by Weight |
|---|---|
| A mixture of higher Molecular esters, mainly mixed esters of pentaerythritol fatty acid ester and citric acid fatty alcohol ester Dehymuls E ® Dehydag | 7.0 |
| Decyl oleate | 10.0 |
| Vaseline ® | 10.0 |
| Lanolin | 5.0 |
| Boric Acid | 0.2 |
| Talc | 12.0 |

-continued

| Baby Cream | Parts by Weight |
|---|---|
| Zinc oxide | 8.0 |
| Nipagin M | 0.2 |
| Product B | 8.0 |
| Water | 39.6 |

EXAMPLE 3

| Night Cream | Parts by Weight |
|---|---|
| Colloidally dispersed mixture of 90 parts of cetylstearyl alcohol and 10 parts of sodium sulfate | 10.0 |
| 2-octyldodecanol | 12.0 |
| Vegetable oil | 7.0 |
| Lanolin | 2.0 |
| Glycerol | 1.0 |
| Product H | 10.0 |
| Nipagin M | 0.2 |
| Perfume oil | 1.0 |
| Water | 56.8 |

EXAMPLE 4

| Boro-glycerol cream | Parts by Weight |
|---|---|
| Colloidally dispersed mixture of 90 parts of cetylstearyl alcohol and 10 parts of sodium lauryl sulfate | 12.0 |
| 2-octyldodecanol | 8.0 |
| Vegetable oil | 5.0 |
| Boric acid | 2.0 |
| Glycerol | 28.0 |
| Nipagin M | 0.2 |
| Product J | 6.0 |
| Water | 38.8 |

EXAMPLE 5

| Moisture cream | Parts by Weight |
|---|---|
| Mixture of mono- and diglycerides of palmitic and stearic acid, Eumulsan MD ® Dehydag | 16.0 |
| Fatty alcohol polyglycol ether, Eumulgin B 3 ® Dehydag | 4.0 |
| Decyl oleate | 5.0 |
| Vegetable oil | 5.0 |
| Paraffin oil | 2.0 |
| Product A | 5.0 |
| 1,2-propylene glycol | 5.0 |
| methyl p-hydroxybenzoate | 0.2 |
| Water | 57.8 |

EXAMPLE 6

| Moisture cream | Parts by Weight |
|---|---|
| Self-emulsifying mixture of mono- and diglycerides of higher saturated fatty acids Eumulsan KD ® Dehydag | 16.0 |
| Fatty alcohol polyglycol ether Eumulgin B 3 ® Dehydag | 1.0 |
| 2-octyldodecanol | 12.0 |
| Isopropyl myristate | 8.0 |
| Paraffin oil | 4.0 |
| Product C | 5.0 |
| Sorbitol solution Karion ®, liquid | 8.0 |
| methyl p-hydroxybenzoate | 0.2 |
| Water | 55.8 |

EXAMPLE 7

| Moisture emulsion | Parts by Weight |
|---|---|
| Mixture of mono- and diglycerides of palmitic- and stearic acid, Eumulsan MD ® Dehydag | 6.0 |
| Fatty alcohol polyglycol ether, Eumulgin B 3 ® Dehydag | 4.0 |
| 2-octyldodecanol | 10.0 |
| Vegetable oil | 4.0 |
| Paraffin oil | 4.0 |
| Product D | 5.0 |
| 1,2-propylene glycol | 7.0 |
| methyl p-hydroxybenzoate | 0.2 |
| Water | 59.8 |

EXAMPLE 8

| Sun protection cream | Parts by Weight |
|---|---|
| Mixture of higher molecular esters with fatty substances Dehymuls K ® Dehydag | 30.0 |
| Decyl oleate | 15.0 |
| Light protection agent | 5.0 |
| Nipagin M | 0.2 |
| Product G | 8.0 |
| Water | 41.8 |

EXAMPLE 9

| Face Mask | Parts by Weight |
|---|---|
| Mixture of fatty acid partial glyceride emulsifiers Cutina LE ® Dehydag | 12.0 |
| Decyl oleate | 4.0 |
| Vitamin oil | 5.0 |
| Kaolin | 2.0 |
| Rice Starch | 3.0 |
| Nipagin M | 0.2 |
| Product E | 10.0 |
| Water | 63.8 |

EXAMPLE 10

| After-shave lotion | Parts by Weight |
|---|---|
| Oleyl/cetyl alcohol | 1.0 |
| Ethanol 96% | 67.5 |
| Methanol | 0.2 |
| Camphor | 0.2 |
| Peru balsam | 0.1 |
| Perfume | 0.5 |
| Hammamelis extract | 10.0 |
| Boric acid | 0.5 |

| After-shave lotion -continued | Parts by Weight |
|---|---|
| Product B | 5.0 |
| Product F | 5.0 |
| Water | 10.0 |

EXAMPLE 11

| Face lotion | Parts by Weight |
|---|---|
| Cucumber juice | 15.0 |
| Citric acid | 0.2 |
| Ethanol 96% | 15.0 |
| Product C | 5.0 |
| Product A | 5.0 |
| Perfume | 1.0 |
| Water | 58.8 |

EXAMPLE 12

| Foam bath | Parts by Weight |
|---|---|
| Monoethanolamine lauryl sulfate, containing approximately 33% active washing substances | 66.0 |
| Coconut fatty acid diethanolamide | 3.0 |
| Product B | 10.0 |
| Perfume oil | 3.0 |
| Water | 18.0 |

EXAMPLE 13

| Cream foam bath | Parts by Weight |
|---|---|
| Sodium lauryl ether sulfate, containing approximately 30% active washing substance | 78.0 |
| Oleic acid diethanolamide | 4.0 |
| Hexyl laurate | 8.0 |
| Product A | 5.0 |
| 1,2-propylene glycol | 2.0 |
| Perfume oil | 3.0 |

EXAMPLE 14

Soap containing agents for keeping the skin moist

A mixture of 80% of sodium tallow soap and 20% of sodium coconut soap was used. The soap, in the form of flakes and having a water content of 20% was mixed with 0.2 parts by weight of 1-hydroxyethane-1,1-diphosphonic acid,
10.0 parts by weight of Product J,
3.0 parts by weight of Perfume oil, relative to 100 parts by weight of soap, and was deformed in an extrusion press and pressed to form cakes.

EXAMPLE 15

Syndet cake of soap containing agents for keeping the skin moist

The Syndet cake of this example was based on a mixture of olefin sulfonate and sulfo-succinic ester salt. The disodium salt of a sulfo-succinic acid mono-fatty alcohol ester, produced from the $C_{12}$–$C_{18}$ fraction of a coconut fatty alcohol, was used in preparing the mixture. The olefin sulfonate was derived from a mixture of straight-chain α-olefins having 15 to 18 carbon atoms.

This olefin mixture was produced by sulfonation of 1 mole of olefin with approximately 1.2 moles of gaseous sulfur trioxide diluted with an inert gas, hydrolysis of the raw product of sulfonation with the calculated quantity of caustic soda at a temperature of approximately 100° C., and bleaching of the sulfonate by means of hypochlorite. The mixture of the two sulfonates contained approximately 5 percent by weight of neutral salts (sodium sulfate and sodium chloride) relative to the anhydrous sulfonate. The Syndet composition contained the following ingredients:

70 parts by weight of a surfactant mixture of
  60 percent by weight of the olefin sulfonate and
  40 percent by weight of the disodium salt of the sulfo-succinic acid ester
15 parts by weight of stearic fatty acid (iodine number 2)
2 parts by weight of lanolin
5 parts by weight of water
8 parts by weight of Product I
2 parts by weight of perfume oil.

The Syndet composition was deformed in an extrusion press and pressed to form cakes.

In place of the compounds used in accordance with the invention mentioned in the above examples, others of the products in accordance with the invention may be used with equally good success.

The preceding specific embodiments are illustrative of the practice of the invention. It is to be understood, however, that other expedients known to those skilled in the art, or given herein, may be employed without departing from the spirit of the invention or the scope of the appended claims.

We claim:

1. In a method for keeping the skin of a warm-blooded animal moist comprising topically applying to the skin an effective moisturizing amount of a cosmetic composition,
wherein the improvement comprises the cosmetic composition containing from 1 to 20 percent by weight, based upon the weight of the total cosmetic composition, of at least one skin moisturizing compound having the formula

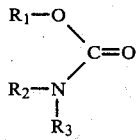

wherein $R_1$ is a member selected from the group consisting of alkyl having 1 to 4 carbon atoms, alkylol having 2 to 4 carbon atoms, and alkyldiol having 3 to 4 carbon atoms, $R_2$ is a hydroxyalkyl having 2 to 6 carbon atoms and having 1 to 5 hydroxyl groups, and $R_3$ is a member selected from the group consisting of hydrogen, alkyl having 1 to 4 carbon atoms, and hydroxyalkyl having 2 to 4 carbon atoms.

2. The method of claim 1, wherein the cosmetic composition comprises from 3 to 10 percent by weight, based upon the weight of the total cosmetic composition, of at least one moisturizing compound.

3. The method of claim 1, wherein the pH value of the cosmetic composition is in the range of acid to neutral.

4. The method of claim 1, wherein the pH value of the cosmetic composition is about 6.

5. The method of claim 1, wherein the cosmetic composition contains conventional cosmetic excipients selected from the group consisting of an emulsifier, a fatty substance, a vegetable extract, a preservative, a perfume, a thickener, a solvent, a surfactant, and mixtures thereof.

6. The method of claim 1, wherein at least one skin moisturizing compound is selected from the group consisting of N-(2-hydroxyethyl)-carbamide acid-2-hydroxyethyl ester, N-(2-hydroxypropyl)-carbamide acid-2-hydroxyethyl ester, N-(1-hydroxy-2-methyl-2-propyl)-carbamide acid-2-hydroxyethyl ester, N-(2-hydroxyethyl)-carbamide acid-1-hydroxy-2-propyl ester, and N-(2-hydroxypropyl)-carbamide acid-1-hydroxy-2-propyl ester.

7. The method of claim 1, wherein the cosmetic composition is a foam bath.

8. In a method for keeping the skin of a warm-blooded animal moist comprising topically applying to the skin an effective moisturizing amount of a cosmetic composition,
wherein the improvement comprises the cosmetic composition consisting essentially of an emulsion adjusted to a pH between 5 and 7 containing an emulsifier and from 1 to 20 percent by weight, based upon the weight of the total cosmetic composition, of at least one skin moisturizing compound having the formula

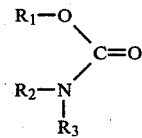

wherein $R_1$ is a member selected from the group consisting of alkyl having 1 to 4 carbon atoms, alkylol having 2 to 4 carbon atoms, and alkyldiol having 3 to 4 carbon atoms, $R_2$ is a hydroxyalkyl having 2 to 6 carbon atoms and having 1 to 5 hydroxyl groups, and $R_3$ is a member selected from the group consisting of hydrogen, alkyl having 1 to 4 carbon atoms, and hydroxyalkyl having 2 to 4 carbon atoms, said emulsion being an oil-in-water emulsion or water-in-oil emulsion.

9. In a method for keeping the skin of a warm-blooded animal moist comprising topically applying to the skin an effective moisturizing amount of a cosmetic composition,
wherein the improvement comprises the cosmetic composition consisting essentially of a water and lower alcohol solution adjusted to a pH between 5 and 7 containing from 1 to 20 percent by weight, based upon the weight of the total cosmetic composition, of at least one skin moisturizing compound having the formula

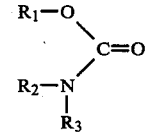

wherein $R_1$ is a member selected from the group consisting of alkyl having 1 to 4 carbon atoms, alkylol having 2 to 4 carbon atoms, and alkyldiol having 3 to 4 carbon atoms, $R_2$ is a hydroxyalkyl having 2 to 6 carbon atoms and having 1 to 5 hydroxyl groups, and $R_3$ is a member selected from the group consisting of hydrogen, alkyl having 1 to 4 carbon atoms, and hydroxyalkyl having 2 to 4 carbon atoms.

10. In a method for keeping the skin of a warm-blooded animal moist comprising topically applying to the skin an effective moisturizing amount of a cosmetic composition,
wherein the improvement comprises the cosmetic composition containing from 1 to 20 percent by weight, based upon the weight of the total composition, of at least one skin moisturizing compound having the formula

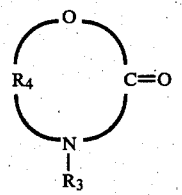

wherein $R_4$ is alkylene having 2 to 4 carbon atoms in its chain or alkylene having 2 to 4 carbon atoms in its chain which is substituted by lower alkyl, lower hydroxyalkyl or lower alkyl and lower hydroxyalkyl and $R_3$ is a member selected from the group consisting of hydrogen, alkyl having 1 to 4 carbon atoms, and hydroxyalkyl having 2 to 4 carbon atoms.

11. The method of claim 10, wherein at least one skin moisturizing compound is selected from the group consisting of 4,4-dimethyl-oxazolidine-2-one, 4-hydroxymethyl-4-methyl-oxazolidine-2-one, 4,4-bis-hydroxymethyl-oxazolidine-2-one, and N-(2-hydroxyethyl)-oxazolidine-2-one.

12. The method of claim 10, wherein the cosmetic composition consists essentially of an emulsion adjusted to a pH between 5 and 7 containing an emulsifier and from 1 to 20 percent by weight, based upon the weight of the total cosmetic composition, of at least one skin moisturizing compound having the formula

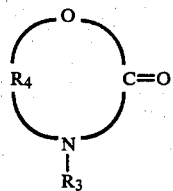

wherein $R_4$ is alkylene having 2 to 4 carbon atoms in its chain or alkylene having 2 to 4 carbon atoms in its chain which is substituted by lower alkyl, lower hydroxyalkyl or lower alkyl and lower hydroxyalkyl, and $R_3$ is a member selected from the group consisting of hydrogen, alkyl having 1 to 4 carbon atoms, and hydroxyalkyl having 2 to 4 carbon atoms, said emulsion being an oil-in-water emulsion or water-in-oil emulsion.

13. The method of claim 10, wherein the cosmetic composition consists essentially of a water and lower alcohol solution adjusted to a pH between 5 and 7 containing from 1 to 20 percent by weight, based upon the weight of the total cosmetic composition, of at least one skin moisturizing compound having the formula

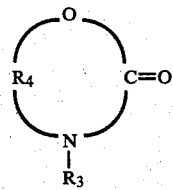

wherein $R_4$ is alkylene having 2 to 4 carbon atoms in its chain or alkylene having 2 to 4 carbon atoms in its chain which is substituted by lower alkyl, lower hydroxyalkyl or lower alkyl and lower hydroxyalkyl, and $R_3$ is a member selected from the group consisting of hydrogen, alkyl having 1 to 4 carbon atoms, and hydroxyalkyl having 2 to 4 carbon atoms.

* * * * *

UNITED STATES PATENT AND TRADEMARK OFFICE
CERTIFICATE OF CORRECTION

PATENT NO. : 4,382,765
DATED : May 10, 1983
INVENTOR(S) : HINRICH MÖLLER et al.

It is certified that error appears in the above—identified patent and that said Letters Patent is hereby corrected as shown below:

Column 8, line 34, "10 parts of sodium sulfate" should read

-- 10 parts of sodium lauryl sulfate --.

Signed and Sealed this

Eighteenth Day of October 1983

[SEAL]

Attest:

Attesting Officer

GERALD J. MOSSINGHOFF

Commissioner of Patents and Trademarks